United States Patent [19]

Clark et al.

[11]   4,191,218

[45]   Mar. 4, 1980

[54] FABRICS FOR HEART VALVE AND VASCULAR PROSTHESES AND METHODS OF FABRICATING SAME

[75] Inventors: Richard E. Clark, St. Louis, Mo.; John Skelton, Sharon; Robert B. Davis, Framingham, both of Mass.

[73] Assignees: Albany International Corp., Albany, N.Y.; Washington University, St. Louis, Mo.

[21] Appl. No.: 901,085

[22] Filed: Apr. 28, 1978

Related U.S. Application Data

[60] Division of Ser. No. 790,442, Apr. 25, 1977, which is a continuation-in-part of Ser. No. 771,359, Feb. 23, 1977, abandoned, which is a continuation-in-part of Ser. No. 575,438, May 7, 1975, abandoned.

[51] Int. Cl.² .................... D03D 7/00; D03D 3/02; A61F 1/22; D04C 1/00
[52] U.S. Cl. ................... 139/383 R; 139/387 R; 139/420 R; 3/1.4; 28/155; 87/7; 87/8
[58] Field of Search ............ 139/383 R, 387 R–390, 139/420 R, 421; 3/1.4, 1.5; 28/155, 156, 167, 142; 87/2.8, 9, 7

[56]   References Cited

U.S. PATENT DOCUMENTS

| 2,836,181 | 5/1958 | Tapp | 87/9 UX |
|---|---|---|---|
| 2,978,787 | 4/1961 | Liebig | 3/1.4 |
| 2,990,605 | 7/1961 | Demsyk | 28/167 X |
| 3,011,527 | 12/1961 | Corbiere | 139/387 R |
| 3,096,560 | 7/1963 | Liebig | 139/387 R |
| 3,130,418 | 4/1964 | Head et al. | 139/387 R |
| 3,409,960 | 11/1968 | Dusenbury et al. | 28/155 |
| 3,429,219 | 2/1969 | Wood, Jr. | 87/8 X |
| 3,588,920 | 6/1971 | Wesolowski | 3/1.4 |

FOREIGN PATENT DOCUMENTS

| 46-42064 | 12/1971 | Japan | 28/155 |
|---|---|---|---|
| 768542 | 2/1957 | United Kingdom | 87/8 |

*Primary Examiner*—James Kee Chi
*Attorney, Agent, or Firm*—Kenway & Jenney

[57]   ABSTRACT

Prostheses for inadequate or diseased heart valves and blood vessels, formed of fabrics comprising multifilament synthetic yarns. For a heart valve the fabric is supported on a three-lobed frame. During manufacture, the fabric is subjected to a plural step compressive shrinking and crimping process to impart nonisotropic elastic compliance approximating the natural mechanical properties. The resulting composite structures are free of thrombogenic complications.

12 Claims, 11 Drawing Figures

FABRICS FOR HEART VALVE AND VASCULAR PROSTHESES AND METHODS OF FABRICATING SAME

The invention described herein was made in the course of work under a grant or award from the Department of Health, Education and Welfare.

This application is a division of copending application Ser. No. 790,442, filed Apr. 25, 1977, the latter being a continuation-in-part of application Ser. No. 771,359, filed Feb. 23, 1977 (now abandoned), which was a continuation-in-part of application Ser. No. 575,438 filed May 7, 1975 and also now abandoned.

BACKGROUND OF THE INVENTION

This invention relates generally to cardiovascular prostheses formed of synthetic fabrics. More particularly, it relates to such fabrics comprising multifilament synthetic yarns, to their manufacture, and to tubular vascular prostheses and trileaflet heart valve replacements formed of such fabrics.

The principal objects of the invention are to provide synthetic structures having a useful life of many flex cycles, to duplicate as closely as possible the mechanical properties of natural heart valves and blood vessels, and to avoid the introduction of blood clotting conditions.

The replacement of heart valves with prostheses has become a standard surgical technique. However, the prostheses currently in use do not entirely satisfy the above objects. Currently, most prosthetic heart valves rely for closure on the sealing of a ball or a flap against a gasket ring. With this construction the ball or flap is situated within the flow channel when lifted away from the gasket in the flow configuration. This is disadvantageous in two important respects. First, the pressure drop across the valve during the open or flow condition is greater than the pressure drop across the natural valve which causes a slight, but continuous and cumulative overload on the heart. Second, the presence of the ball or flap creates regions of turbulent flow tending to damage the red blood cells.

With the foregoing disadvantages in mind, research has been directed to developing leaflet valves more closely approximating the structure and functions of the human valve. The latter comprises then, flexible membranes that fold outward into the surrounding blood vessel in the open configuration, thus causing a minimum of disturbance to the flowing blood. In the closed configuration the leaflets form three contiguous pouches that are held in close and leak-proof contact by the pressure of the blood. As a result of the extreme lightness and flexibility of the leaflets the valve has a short response time, passing quickly from the fully closed to the fully open state, with the result that there is little energy loss in the flowing blood and a minimum of undesirable regurgitation.

These functional characteristics of the human valve result from the composite structure of the natural leaflet. This comprises an arrangement of bundles of collagen fibers embedded in a softer tissue material. The composite structure gives the leaflet good load bearing capacity, a high resistance to tear and sufficient softness and flexibility to make a good seal in the closed configuration. At the peak of the pressure pulse, the leaflet withstands a load exceeding 150 gm/cm along a line therein normal to the load.

Heart valve tissue is also anisotropic in its elastic properties, that is, the load-deformation characteristic in one direction is different from that in another direction. It has been found useful to define two particular directions for purposes of this description. These directions are parallel and perpendicular to the free edge of the leaflet, and correspond respectively to the circumferential and radial directions commonly referred to in the literature.

In the direction parallel to the free edge the natural leaflet extends very readily with increased load until an elongation of ten to twelve percent is reached at a load of one to two grams per centimeter of leaflet width. Upon further increase in load the resistance to further elongation increases greatly. In the direction perpendicular to the free edge the region of easy extension with increased load continues to approximately 20 percent elongation, at which the load is about 2 gm/cm. Upon further increases in load the resistance to further elongation, though greater than in the initial region, is not as high as it is in the parallel direction.

A recent development involves the use of stabilized pig heart valves as replacements for failing human valves. These valves embody some of the characteristics of human valves discussed above. However the collection, grading, sterilizing, fixing and storing of pig valves is complicated and costly. In consequence, a clear need has been realized for a trileaflet heart valve made entirely from synthetic materials.

SUMMARY OF THE INVENTION

According to this invention, replacement heart valves and vascular prosthetic devices are formed of fabrics woven of multifilament polymeric yarns which are mutually separated by interstices in the woven pattern. The fabric is compressively shrunk, that is, compacted in a first direction to form crimps in the yarns, the crimps being formed and heat set to lie in planes generally parallel with the fabric, and the yarns are bloomed in the interstices to form spaced of varying sizes and orientations between the filaments. This compressive shrinking step is then repeated in a second direction forming an angle with the first direction.

Preferably, the fabrics are woven either in the form of ribbons having a selvage of uncut yarns, this selvage forming the free edge of the heart valve leaflet, or as tubing for vascular replacements.

A fabric ribbon so formed may be inserted into a frame of three-lobed configuration, this frame supporting the leaflets in proper orientation and providing a means to facilitate suturing to the wall of the surrounding blood vessel.

The foregoing and other features of the invention are described more fully in the following description with reference to the appended drawings.

DRAWINGS

DESCRIPTION

Figure 10:
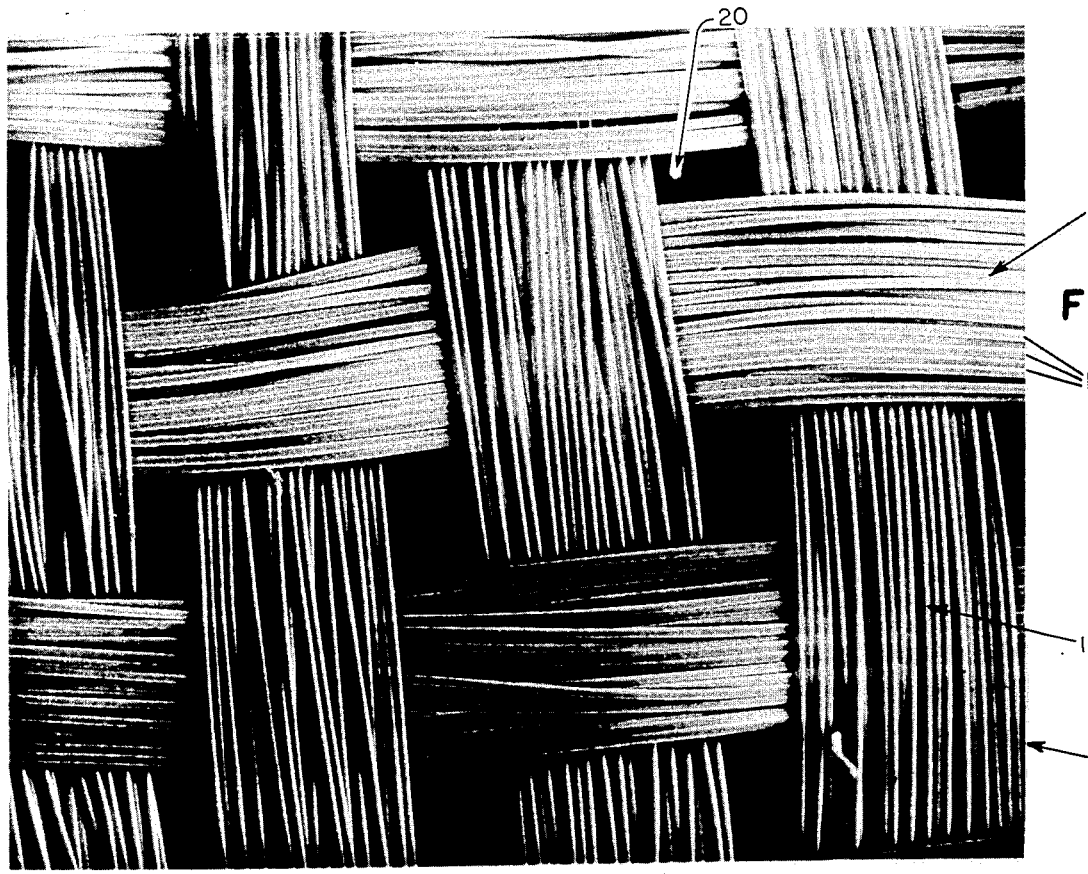
FIG. 10 is a photograph showing a plain woven multifilament polymeric fabric prior to compressive shrinking.

Referring to the drawings, FIG. 10 shows one form of starting fabric 12 having warp yarns 14 and weft yarns 16. The warp and weft yarns are each formed of untwisted filaments 18 of a polyester, for example, polyethylene terephthalate. For illustration, the fabric may be woven with approximately 100 yarns per inch in each direction, the yarns being about 30 denier. Each yarn contains 30 filaments 18, each filament having a diameter of about 10 microns. Because the yarns have no twist, as shown in the woven form of FIG. 10 they have a flattened configuration. Consequently, the fabric is only about 3 to 4 filament-diameters thick. Also, as further explained below, the fabric is preferably woven with at least one selvage having no cut yarns. For this reason the fabric is advantageously woven in the form of a ribbon, although this is not a necessity.

Commercially available polyester yarn generally contains a number of impurities that make it potentially damaging to the body if used in implanted prosthetic devices. These impurities include residual catalyst from the polymerization process, oligomers, antioxidants and other stabilizers, delusterant and surface finishes. Accordingly, it is preferred to employ a pure polymeric material.

As shown in FIG. 10, the yarns 14 and 16 are woven so as to provide interstices 20. These interstices have a role in the subsequent shrinking and crimping process steps described below, which are performed on the fabric of FIG. 10 to produce the bilaterally crimped form shown in FIG. 11. In successive steps, the fabric is shrunk in two directions by compacting it while subject to in-plane compressive stress, each step being substantially as described for example in U.S. Pat. No. 3,001,262 dated Sept. 26, 1961, to Charles Schwabe Parker and Alexander Melville. A machine may be used similar to that described in U.S. Pat. Nos. 2,765,513 and 2,765,514, both dated Oct. 9, 1956, and both to Richard R. Walton. The shrinking steps produce crimps in the yarns and cause them to bloom or spread out in the interstices of the woven pattern.

In order to produce the desired easy stretch characteristics in both directions, similar to those of the natural valve leaflet, the same woven fabric is compacted in both the warp and weft yarn directions sequentially. In this respect, the present process is in contrast to the technique described in the above patent to Parker et al, wherein the yarns of a first woven fabric are crimped in the warp direction, the fabric is then unravelled and the warp yarns are used as the weft or filling yarns of a subsequently-woven fabric, the latter still later being crimped in the warp direction to give a two-way stretch characteristic. As a result of the present process the crimps in the yarns in both the warp and weft directions are formed and heat set to lie in planes generally parallel with the fabric, and the yarns are bloomed in the interstices to form spaces of varying sizes and orientations between the filaments. A substantial number of these latter spaces have dimensions in a preferred range of 20 to 40 microns, and are produced in an even distribution throughout the fabric. Thus the completed fabric is relatively thin as compared with the final fabric of Parker et al wherein the crimps and bloomed filaments of the final weft or filling yarns are necessarily displaced and reoriented during the second weaving relative to the plane of the fabric and the interstitial locations in the final weave.

The desirability of a thin fabric over a thicker one has been recognized as the result of the functional characteristics desired, in particular the flexibility and stretch characteristics, the non-thrombogenic property and the capability of withstanding many millions of flex cycles without fatigue failure. Non-thrombogenic properties are imparted to the fabric described herein so that the flowing blood is in contact only with naturally-occurring, compatible surfaces. Thus the filaments in the fabric become analogous to the bundles of collagen fibers in the natural leaflet, and provide a textile scaffold or lattice onto which the body can deposit tissue to provide the membrane function of the leaflet at the fabric-blood interface, the tissue ingrowth is such that the clot is firmly anchored to the fabric and does not break free into the bloodstream. Thus the fabric becomes completely embedded in a layer of living tissure that is thin enough to be nourished by diffusion processes.

For effective use as a heart valve leaflet the fabric must have a region of very easy extension up to elongation levels in the range of 10 percent to 20 percent. In particular, as will be evident from the following description of FIGS. 1 to 8, each leaflet in the closed configuration is subjected to bending over a relatively sharp radius along a line perpendicular to its free edge. Along this line there is a region of high stress concentration.

Figure 11:
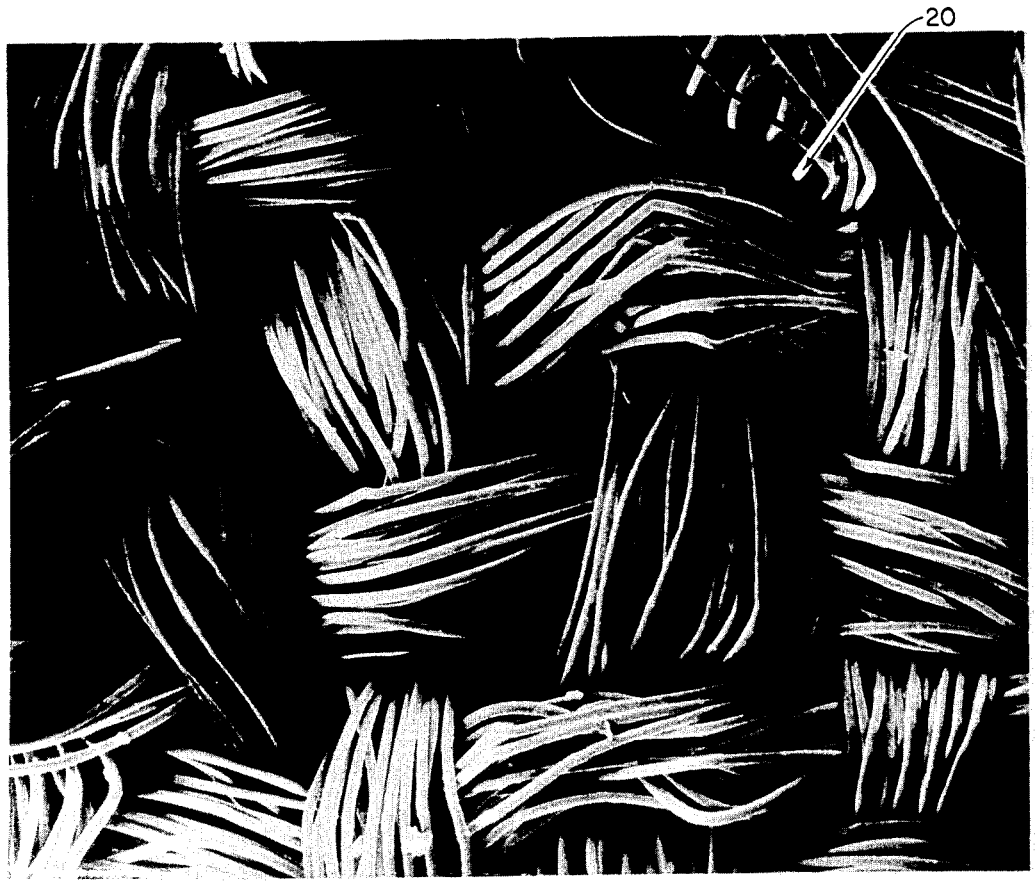
FIG. 11 is a photograph showing the fabric of FIG. 9 after compressive shrinking in the warp and weft directions.

An additional advantage of the present method is illustrated by FIG. 11 wherein it will be noted that the individual yarns are bloomed in the interstices 20; that is, the filaments are opened up locally in these interstices to provide a distributed matrix of smaller interstices of varying sizes and orientations. In contrast, the precursor fabric such as that of FIG. 10 has a regular configuration of spaced holes of relatively larger, fixed dimensions.

The fabric manufactured according to the present process has been tested for tissue ingrowth, and has been shown to have performance superior in this respect to other available fabrics. It can be produced with the specific elongation characteristics needed for the leaflet application, and moreover such elongation characteristics may differ in two directions, such as the warp and weft directions.

The following is a more detailed description of the creping or compacting method employed according to this invention. Using the machine described in the above-mentioned U.S. Pat. Nos. 2,765,513 and 2,765,514, a ribbon of the woven fabric shown in FIG. 10, approximately one and one-half inches wide and six inches long is placed between two sheets of paper and passed through the bite between a top roll and a bottom roll in the warp-wise direction. The top roll has a surface speed of 5.3 ft/sec and the bottom roll has a surface speed of 1.1 ft/sec. During this compacting run the warp threads are shrunk or compacted to form crimps, these crimps being forced by the applied pressure of the rolls to lie in planes generally parallel with the fabric. At the same time the filaments of the warp threads are spread apart in the interstices between the weft yarns; that is, the yarns bloom in these interstices, thereby forming spaces of varying sizes and orientations, as shown in FIG. 11. Upon completion of this compacting step the fabric is removed from the paper sheets.

A second compacting run is then performed in a substantially identical manner to that described above, except that the fabric piece is passed through the bite of the rolls in the weft-wise direction.

If desired, each of the above-described compacting runs may be repeated, in which case the ribbon is preferably rotated through 90 degress after each run.

The compaction steps in the two directions may be varied as to number and degree of compaction to produce the desired load-elongation characteristic in each of the two directions, thus approximating the corresponding characteristics of the natural leaflet. In any case, the compaction steps are such as to produce very easy extension up to elongational levels of 10 to 20 percent.

After the series of compacting runs, the fabric is heat set while in an unstressed state at a temperature below the fusion temperature. For polyethylene terephthalate a temperature of 410 degrees F. may be used, for example. The heat setting is preferably performed in a circulating hot air oven, and a typical time duration is one and one-half minutes.

In some cases it is desirable to treat the yarn prior to weaving in order to prevent damage to the filaments during the weaving process. A suitable method of treatment is a coating of 5 percent solution of polyvinyl alcohol. After weaving, this additive is washed out of the fabric in an aqueous wash.

Figure 1:
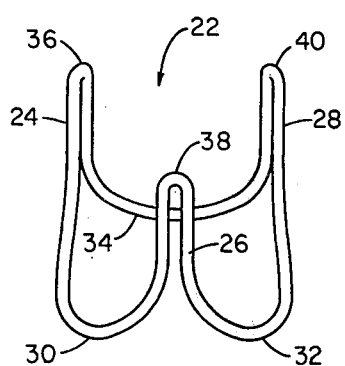
FIG. 1 shows the main frame of the preferred form of the heart valve.
Figure 4:
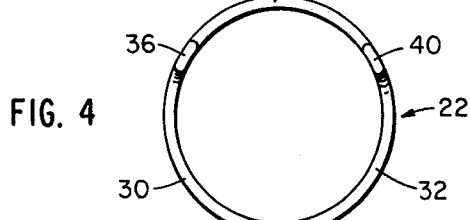
FIG. 4 is a top plan view of the frame shown in FIG. 1.
Figure 5:
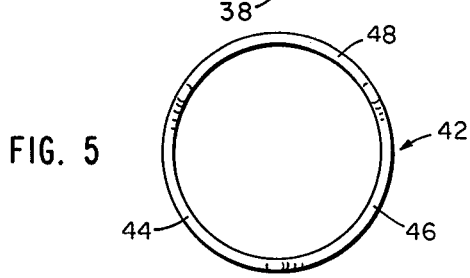
FIG. 5 is a top plan view of the frame shown in FIG. 3.

We turn next to a description of the preferred form of trileaflet heart valve replacement. Referring to FIG. 1, there is shown a main frame 22 comprising a single length of 0.1 cm. diameter round polypropylene rod bent into a form having three mutually equidistant, generally parallel legs 24, 26 and 28, each leg comprising a pair of rod portions slightly spaced apart, the rod portions being connected at one end and diverging at the other end. The diverging rod portions form three lobes 30, 32 and 34. The connected ends of the rod portions in each pair form bights 36, 38 and 40. FIG. 4 is a top plan view of the main frame 22.

Figure 7:
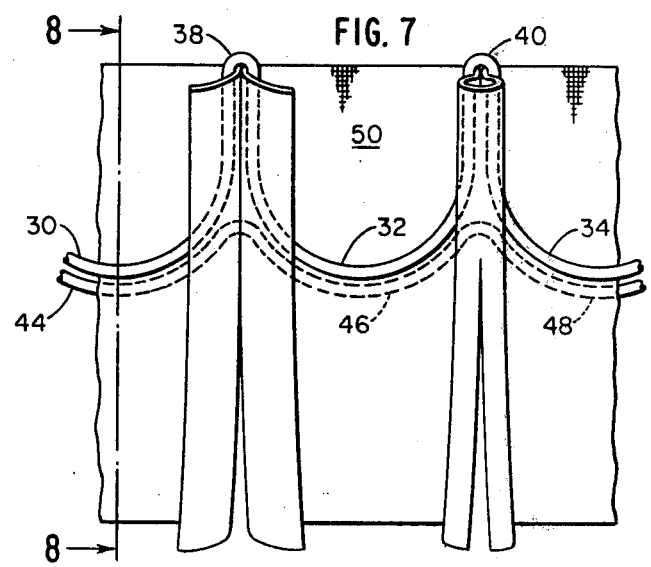
FIG. 7 is a developed view of the partially constructed heart valve, corresponding to FIG. 6.

A second frame 42 (FIGS. 3 and 5) is formed of a single length of 0.1 cm. diameter round polypropylene rod bent into a form having three lobes 44, 46 and 48 generally congruent with the lobes 30, 32 and 34 so as to fit in close contact therewith as shown in FIG. 7.

Figure 2:
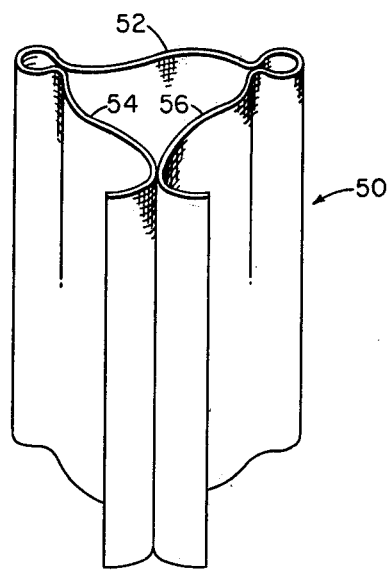
FIG. 2 shows a fabric ribbon in the configuration formed by inserting it into the main frame between the rod portions of its legs.

The assembly is started by threading a bilaterally crimped and compacted ribbon 50, produced by the method described above and appearing as in FIG. 11, through the three pairs of legs so as to produce the configuration shown in FIG. 2. The frame 22 is shown in FIG. 1 in exploded relation to FIG. 2 for clarity of illustration. The upper selvage has no uncut yarns and forms the free edges 52, 54 and 56 of valve leaflets.

Figure 6:
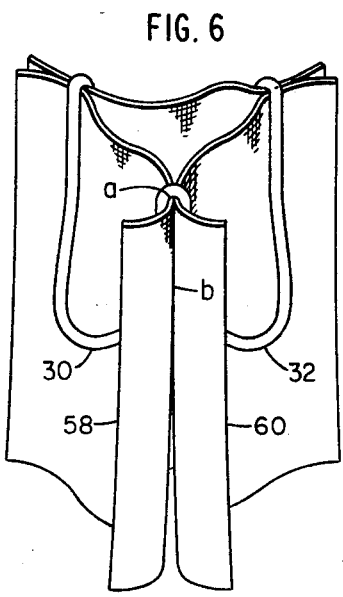
FIG. 6 shows the partially fabricated heart valve with the fabric inserted into the main frame and cut open preparatory to cementing thereto.

Thus a double layer of the fabric is passed through each pair of rod portions forming one of the legs 24, 26 and 28. It is necessary to attach the fabric firmly to these legs, and also to the connecting lobes 30, 32 and 34. To facilitate this attachment, the fabric is preferably cut lengthwise externally of each leg as shown in FIG. 6. Referring to FIG. 6, adhesive such as polyurethane dissolved in tetrahydrofuran is applied to attach the fabric to each of the legs as follows. Flaps such as 58 and 60 are spread apart and the adhesive is applied at the external point of juncture of the flaps where they enter between the rod portions, in a continuous line extending between points a and b. The adhesive material reaches to the external surfaces of the frame by penetration through the fabric flaps along this line; that is, the adhesive contacts the rod portions of the frame only on their outer surfaces. The leaflets comprise only those portions of the fabric on the inside of the frame, and these portions are not penetrated by the adhesive. Thus local stiffening and resultant flex failure caused by such adhesive penetration is avoided.

The above method of adhesive application also distributes the stresses of flexure evenly along the margins of the leaflets, and avoids excessive stress concentrations. The margins are permitted to move upon each flexure over the rounded contours of the surfaces of the rod portions that are located on the inside of the frame, and that are not penetrated by the adhesive.

Figure 8:
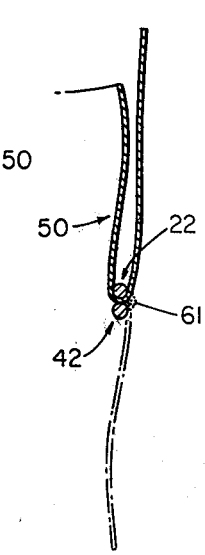
FIG. 8 is a cross-sectional view taken on line 8—8 in FIG. 7.
Figure 3:
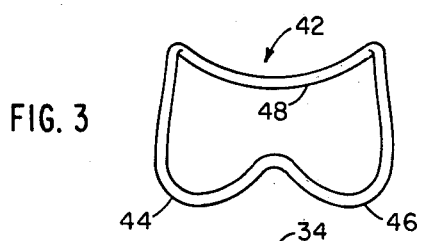
FIG. 3 shows the second frame.

The attachment of the fabric to the lobes 30, 32 and 34 is next accomplished by first placing the second frame 42 adjacent these lobes with the fabric pieces passing therebetween as shown in FIGS. 7 and 8. Adhesive 61 is then applied through the fabric and to the surfaces of both the main frame 22 and the second frame 42, in a continuous line extending between the points b of the respective legs and connecting these three points. As in the previous step, the adhesive material preferably does not penetrate any portion of the leaflet material lying within the main frame 22, and remains out of contact with blood passing through the valve.

The foregoing steps essentially complete the fabrication of the leaflet portions of the valve. The remaining steps of fabrication are for the purpose of facilitating the suturing of the prosthesis within the blood vessel. The excess fabric available on the outside of the frame can be rolled and consolidated along the junction line between the main and second frames to provide attachment points for stitches during surgical insertion.

The frame material is preferably polypropylene, although other materials have also been employed with success. Polypropylene has excellent flex endurance and chemical stability, but is difficult to attach by adhesive to other materials. To facilitate adhesion, the main and second frames 22 and 42 may be encapsulated with polyurethane by multiple dip coating. The resulting encapsulated frame components have proved to demonstrate the desired characteristics of polypropylene without structural failures or breakdowns at the adhesive junctures.

Valves employing the fabric described above have been tested in an accelerated fatigue tester to assess their long-term endurance characteristics. Fatigue failures so induced have generally occurred in the region of greatest fabric flexure, that is, along a line in each leaflet that is perpendicular to its free edge and substantially equidistant between the contiguous legs. The failures have generally occurred by breakdown of the filaments in the yarns running parallel to the free edge of the leaflets. As a means of providing greater fabric strength along the last-mentioned lines, woven fabrics may be provided with a greater number of load-bearing yarns in this direction. However, there is a limit to the increase that is possible using the plain woven pattern of FIG. 10 without seriously disturbing the geometry of the fabric interstices.

Figure 9:
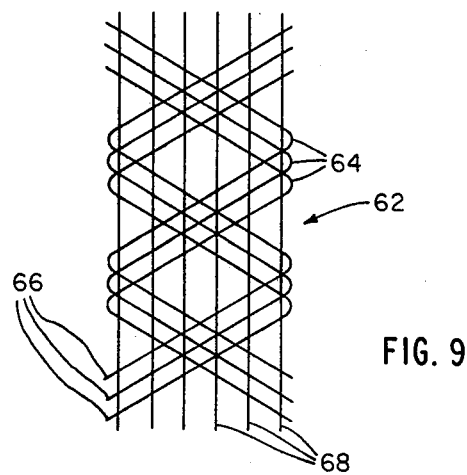
FIG. 9 illustrates a flat braided fabric pattern.

An alternative fabric construction pattern having improved strength against such fatigue failure is illustrated in FIG. 9. The fabric shown is a flat braided ribbon 62 comprising 3 sets of yarns, namely, a first diagonal set 64, a second diagonal set 66 and a longitudinal inlaid set 68. The yarns in each of the three sets are preferably multifilament untwisted yarns similar to those shown in FIG. 10. The ribbon 62 is braided on a conventional flat braiding machine. It will be noted that each selvage has uncut yarns and one of those becomes the free edge of each leaflet. Thus fraying of the free edges of the leaflets is avoided as in the example described above. In this embodiment both of the sets 64 and 66 perform the load-bearing function of a single set of yarns in the earlier-described fabric. The result is that a greater number of yarns have a significant component of load bearing capacity oriented parallel to the free edge.

The fabric 62 of FIG. 9 is preferably formed by braiding the yarn sets 64 and 66 with inlaid longitudinal yarns 68 in a well-known manner, thus producing a type of triaxial fabric. Such flat braided fabrics have an additional advantage over conventionally woven fabrics, in that they are inherently highly extensible in the cross machine direction, that is, in the direction perpendicular to the yarns 68. Such fabrics make it possible to produce a two-way stretch characteristic with any desired combination of stretch capabilities by compacting in the direction of the yarns 68 only.

In the foregoing description, the advantages of the described fabrics have been noted with respect to their use in replacement heart valve leaflets. However, many of the attributes of the fabrics make them ideally suited for other biomedical applications. For example, vascular prostheses, particularly those with small diameters, require a combination of good stretch characteristics and inherent biological inertness. Fabrics essentially similar to those described above have been woven in tubular form and compacted in two directions to impart the necessary two-way stretch characteristics for use as conduits for flowing blood. For example, beginning with a tubular plain woven fabric appearing as in FIG. 10 with the yarns 14 being oriented axially of the tubing, the fabric is compacted by the following steps. A section of the tubing is placed between two pieces of paper, and the first compaction run is carried out in the axial direction. Then, the flattened tubing section is removed from the papers, rotated 90 degrees, reinserted between two pieces of paper and passed through a second compaction run transversely of the axial direction. These compaction steps are repeated, if desired, in successive directions displaced 90 degrees. Subsequently, the tubing is slid onto a glass tube having a diameter chosen to retain it in a round cross section with minimal stress. The glass tube and fabric are then tightly wrapped in several layers of aluminum foil, thus forcing the crimps to lie in planes generally parallel with the fabric surface. The fabric is then heat set for 1½ minutes in a circulating hot air oven at 485 degrees F.

Alternatively, a tubular braided vascular prosthesis similar to the flat braided form shown in FIG. 9 may be produced. In this form, only compaction in the longitudinal direction is required, since the braided tubing has inherent stretch capabilities in directions transverse to the axis.

With either of the above tubular weave patterns, it is emphasized that two-way stretch characteristics are imparted to the vascular prosthetic devices. The radial compliance is particularly useful in avoiding stiffness mismatches at the boundaries between the existing artery and its synthetic replacement, particularly in small diameter arteries. A circumferential extension ratio of 1.5:1 is typically necessary in order to provide the proper match of properties, and this ratio has been provided by the above-described tubular materials.

We claim:

1. A fabric for a cardiovascular prosthesis comprising woven multifilament polymeric yarns extending in first and second directions forming an angle therebetween, the yarns in each of said directions having crimps similarly oriented with respect to the plane of the fabric and being bloomed in their interstices to form a substantial number of open interstitial spaces in the range of 20 to 40 microns evenly distributed throughout the fabric, the stretch characteristic of the fabric having a region of easy elongation up to at least ten percent in at least one of said directions.

2. A fabric according to claim 1, in which the fabric has different elastic compliance in said first and second directions.

3. A fabric according to claim 1, in which the yarns are flattened and essentially untwisted.

4. A fabric according to claim 1, in which said angle is a right angle.

5. A fabric according to claim 1 in the form of a ribbon having a selvage of uncut yarns.

6. A fabric according to claim 1 in the form of a tube.

7. A fabric according to claim 6, in which the longitudinal elastic compliance differs from the circumferential elastic compliance.

8. A fabric according to claim 1, in which the filament diameters are about 10 microns.

9. A fabric according to claim 1, of tubular form and having a circumferential extension ratio of at least 1.5 to one.

10. A fabric according to claim 3, having a thickness less than about four filament diameters.

11. A fabric for a cardiovascular prosthesis comprising a flat braided ribbon having a selvage of uncut multifilament polymeric yarns extending in first and second directions forming an angle therebetween, the yarns in each of said directions having crimps similarly oriented with respect to the plane of the fabric and being bloomed in their interstices to form a substantial number of open interstitial spaces in the range of 20 to 40 microns evenly distributed throughout the fabric, the stretch characteristic of the fabric having a region of easy elongation up to at least ten percent in at least one of said directions.

12. A fabric according to claim 11, having longitudinal yarns extending parallel to the selvage and braid carrier yarns extending to the selvage at acute angles thereto.

* * * * *

UNITED STATES PATENT AND TRADEMARK OFFICE
CERTIFICATE OF CORRECTION

PATENT NO. : 4,191,218
DATED : March 4, 1980
INVENTOR(S) : Richard E. Clark, John Skelton and Robert B. Davis It is certified that error appears in the above-identified patent and that said Letters Patent are hereby corrected as shown below:

Column 1, line 47, cancel "then" and substitute --thin--.

Column 2, line 41, cancel "spaced" and substitute --spaces--.

Column 4, line 27, after "leaflet" insert --and the desired sealing properties.--; lines 27-30, cancel "at the fabric-blood interface, the tissue ingrowth is such that the clot is firmly anchored to the fabric and does not break free into the bloodstream."

Column 7, line 38, cancel "prostneses" and substitute --prostheses--.

Signed and Sealed this

Nineteenth Day of August 1980

[SEAL]

Attest:

SIDNEY A. DIAMOND

Attesting Officer

Commissioner of Patents and Trademarks